United States Patent
Kanbara et al.

(10) Patent No.: US 6,784,317 B2
(45) Date of Patent: Aug. 31, 2004

(54) PRODUCTION OF QUATERNARY AMMONIUM SALT OF HYDROXYCARBOXYLIC ACID AND QUARTERNARY AMMONIUM SALT OF INORGANIC ACID

(75) Inventors: Yutaka Kanbara, Niigata (JP); Yasushi Higuchi, Niigata (JP); Tomoo Tsujimoto, Niigata (JP); Genki Nogami, Niigata (JP)

(73) Assignee: Mitsubishi Gas Chemical Company, Inc, Tokyo (JP)

( * ) Notice: Subject to any disclaimer, the term of this patent is extended or adjusted under 35 U.S.C. 154(b) by 0 days.

(21) Appl. No.: 10/125,371

(22) Filed: Apr. 19, 2002

(65) Prior Publication Data

US 2002/0165409 A1 Nov. 7, 2002

(30) Foreign Application Priority Data

| May 2, 2001 | (JP) | 2001-135339 |
| May 2, 2001 | (JP) | 2001-135340 |
| Jul. 19, 2001 | (JP) | 2001-219740 |
| Jul. 19, 2001 | (JP) | 2001-219741 |

(51) Int. Cl.$^7$ ........................ C07C 211/62; C07C 211/64
(52) U.S. Cl. ........................ 564/296; 564/288
(58) Field of Search ........................ 564/296, 288

(56) References Cited

U.S. PATENT DOCUMENTS 3,190,919 A * 6/1965 Swanson .................. 260/567.6
6,066,763 A * 5/2000 Hayakawa .................. 562/581

FOREIGN PATENT DOCUMENTS

GB     2 067 196 A * 7/1981 ........... C07C/91/26

OTHER PUBLICATIONS

European Search Report, dated Sep. 3, 2002, for EP 02 008898.

Kametani, I, et al., "Novel Methylation III (1a). Methylation of Tertiary Amines such as Pyridine and Isoquinoline with Alkyl Carboxylates (1b)", Journal of Heterocyclic Chemistry, vol. 3, 1996, pp. 129–136.

Abstract for JP 2000 226360, Aug. 15, 2000.

Abstract for JP 11–315055, Nov. 16, 1999.

\* cited by examiner

*Primary Examiner*—Brian Davis
(74) *Attorney, Agent, or Firm*—Antonelli, Terry, Stout & Kraus, LLP

(57) ABSTRACT

A quaternary ammonium hydroxycarboxylate is produced by quaternizing a tertiary amine with a hydroxycarboxylic ester represented by the following Formula 1:

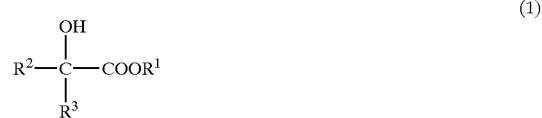

wherein $R^1$ to $R^3$ are as defined in the disclosure. By using only one tertiary amine having at least one substituent different from $R^1$ of the ester moiety of the hydroxycarboxylic ester and by controlling the reaction conditions, a mixture of quaternary ammonium hydroxycarboxylates having different quaternary ammonium ions is produced. By reacting an inorganic acid with the quaternary ammonium hydroxycarboxylate or its mixture, a quaternary ammonium salt of inorganic acid or its mixture is produced.

25 Claims, No Drawings

PRODUCTION OF QUATERNARY AMMONIUM SALT OF HYDROXYCARBOXYLIC ACID AND QUATERNARY AMMONIUM SALT OF INORGANIC ACID

BACKGROUND OF THE INVENTION

1. Field of the Invention

The present invention relates to methods for producing a quaternary ammonium hydroxycarboxylate, a mixture of quaternary ammonium hydroxycarboxylates having different ammonium ions, a quaternary ammonium salt of inorganic acid, and a mixture of quaternary ammonium salts of inorganic acid having different ammonium ions. A quaternary ammonium salt of organic acid has been widely used as a surfactant and is also useful as a raw material for phase transfer catalysts, medicines, and cosmetics. Recently, a highly pure quaternary ammonium salt is demanded in the fields of electronic materials for use as a cleaning agent for electronic parts, a developer of resists, etc. The quaternary ammonium salt is also particularly useful as electrolytes for electric double layer capacitor that has recently come to attract attentions as a battery system for an uninterruptible power supply, a hybrid car, etc. It is known that the cycling characteristics, etc. of electric double layer capacitor are affected by a trace amount of impurities such as water and halogen, and therefore, a quaternary ammonium salt of inorganic acid for use in this field is particularly required to be highly pure.

2. Description of the Prior Art

Alkyl halides and dialkyl sulfates are conventionally known as a quaternizing agent for a tertiary amine. These quaternizing agents are, however, not suitable for use in the manufacture of electronic parts because halogen ion and sulfate ion contaminate the quaternary ammonium salt. Other known quaternizing agents include dialkyl carbonates and organic carboxylic ester. However, these compounds are not industrially suitable because the quaternizing reaction is relatively slow and should be conducted in a polar solvent such as alcohol to prevent the generation of carbon dioxide or carbon monoxide due to the decomposition of dialkyl carbonates and organic carboxylic ester. Thus, no quaternizing agent is known in the art, which enables industrially efficient production of a highly pure quaternary ammonium salt by the quaternization of a tertiary amine in the absence of solvent.

It has been known to produce a quaternary ammonium salt of organic carboxylic acid by the reaction of a quaternary ammonium hydroxide and a carboxylic acid. In another known method, a quaternary ammonium acid sulfate is treated with an alkali hydroxide and a carboxylic acid. However, since the process is complicated, these methods are less practicable for industrial use because of high costs. In addition, the methods fail to produce highly pure products because a small amount of sulfate ion or alkali metal remains in the products.

In still another known method, an quaternary ammonium alkyl carbonate is reacted with an organic carboxylic acid. This method can produce a highly pure quaternary ammonium salt of organic carboxylic acid. However, the process for synthesizing the quaternary ammonium alkyl carbonate from a tertiary amine and a dialkyl carbonate is long, and the method requires a expensive dialkyl carbonate. Therefore, this method is not industrially applicable.

In still another known method, a quaternary ammonium salt of organic carboxylic ester is directly produced by the reaction of a tertiary amine and an organic carboxylic acid. However, the rate of reaction is generally low to require a long reaction time, and the yield of product is not sufficiently high. To solve this problem, is proposed a method for reacting an organic carboxylic ester and a tertiary amine in a polar solvent. For example, Japanese Patent Application Laid-Open No. 62-174036 discloses a method for carrying out the reaction in a polar solvent such as alcohol, amide and nitrile. Japanese Patent Application Laid-Open No. 6-329604 proposes to react an organic carboxylic ester and an tertiary amine in a polar solvent in the presence of a small amount of organic carboxylic acid. However, since the use of the polar solvent and the addition of the organic carboxylic acid are required, these method are not industrially advantageous.

Thus, there has been known no method that is capable of efficiently producing a quaternary ammonium salt of organic carboxylic acid at high yield by the quaternization of a tertiary amine with an organic carboxylic ester in the absence of a polar solvent.

A quaternary ammonium salt of inorganic acid is generally produced by quaternizing a tertiary amine with an alkyl halide to prepare a quaternary ammonium halide that is then converted into a quaternary ammonium salt of inorganic acid by replacing the halide ion with an acid radical of a desired acid. However, this method involves a problem of a portion of the starting halide remaining in the product.

To solve this problem, is known a method of producing a quaternary ammonium salt of inorganic acid by the reaction of an inorganic acid with a quaternary ammonium alkyl carbonate or a quaternary ammonium hydrogencarbonate. Japanese Patent Publication No. 7-116113 discloses a method of producing a quaternary ammonium salt of inorganic acid, which comprises a first step of reacting a tertiary amine with a carbonate ester to obtain a quaternary ammonium carbonate and a second step of converting the quaternary ammonium carbonate to a corresponding quaternary ammonium salt of inorganic acid by mixing with an inorganic acid while removing the generated carbon dioxide gas from the reaction system. This method creates little impurities such as water and halogen. However, according to the working examples thereof, the reaction of triethylamine and dimethyl carbonate of the first step is carried out at a high reaction pressure, 0.5 MPa, for a long reaction time, 12 h. Additionally, the relatively expensive dialkyl carbonate is decomposed to carbon dioxide and alcohol in the second step. Further, if a low-boiling inorganic acid is used to remove the by-produced carbon dioxide from the reaction system, a portion of the inorganic acid is removed together with carbon dioxide.

As mentioned above, the conventionally known methods for producing a quaternary ammonium salt of inorganic acid are carried out at a high pressure for a long reaction time, and have problems of decomposition of the relatively expensive starting dialkyl carbonate into carbon dioxide and alcohol, difficulty of reuse of the starting compound, and easy loss of the starting compound.

A mixture of salts of organic or inorganic acid having different quaternary ammonium ions is generally produced by mixing different quaternary ammonium salts of organic or inorganic acid that are separately produced, or by quaternizing a mixture of starting trialkylamines corresponding to the intended quaternary ammonium salts. These methods, however, require different starting compounds to increase the cost for apparatus and switching operations. In addition, the starting amines having different alkyl groups are generally expensive. Thus, no industrially advantageous method for producing a mixture of salts of organic or inorganic acid having different quaternary ammonium ions is known in the art. As will be described in Comparative Example 1, it was found by the inventors that the relatively expensive dimethyl carbonate was decomposed when the reaction was carried out in the same manner as in the present invention while using dimethyl carbonate that is known as a quaternizing agent, although a mixture of quaternary ammonium salts of organic acid was obtained.

Thus, no industrially advantageous method is known in the art in the production of a mixture of plural salts of organic or inorganic acid having different quaternary ammonium ions from only one starting tertiary amine.

SUMMARY OF THE INVENTION

A first object of the present invention is to provide an industrially advantageous method for producing an quaternary ammonium salt of organic acid.

A second object of the present invention is to provide an industrially advantageous method for producing a mixture of salts of organic acid having different quaternary ammonium ions.

A third object of the present invention is to provide an industrially advantageous method for producing a highly pure quaternary ammonium salt of inorganic acid.

A fourth object of the present invention is to provide an industrially advantageous method for producing a mixture of salts of inorganic acid having different quaternary ammonium ions.

As a result of extensive study on the production method of a quaternary ammonium salt of organic acid by the quaternization of a tertiary amine, the inventors have found that a highly pure quaternary ammonium salt of organic acid is produced in industrially advantageous manner by quaternizing a tertiary amine using a specific hydroxycarboxylic ester as a quaternizing agent even in the absence of a polar solvent.

In addition, as a result of extensive study on the production method of a mixture of salts of organic acid having different quaternary ammonium ions, the inventors have surprisingly found that such a mixture is obtained by a trans-alkylation between only one tertiary amine and a specific hydroxycarboxylic ester under selected reaction conditions.

Further, as a result of extensive study on the production method of a quaternary ammonium salt of inorganic acid, the inventors have found that the quaternization of a tertiary amine by a specific hydroxycarboxylic ester proceeds at a sufficient reaction rate in a first step even at a low pressure and without using a solvent, thereby producing the quaternary ammonium salt of organic acid efficiently, and further found that a highly pure quaternary ammonium salt of inorganic acid is obtained by reacting the quaternary ammonium salt of organic acid with an inorganic acid in a second step without the decomposition of a by-produced hydroxycarboxylic acid.

Still further, as a result of extensive study on the production method of a mixture of salts of inorganic acid having different quaternary ammonium ions, the inventors have found that a mixture of quaternary ammonium hydroxycarboxylates having different quaternary ammonium ions is produced from only one tertiary amine and a specific hydroxycarboxylic ester by selecting the reaction conditions of the above first step, and further found that a mixture of corresponding quaternary ammonium salts of inorganic acid is obtained by reacting the mixture with an inorganic acid in a second step without decomposing the by-produced hydroxycarboxylic acid and without changing the proportion of the starting mixture of quaternary ammonium hydroxycarboxylates.

Thus, in a first aspect of the present invention, there is provided a method for producing a quaternary ammonium hydroxycarboxylate, which comprises a step of reacting a tertiary amine represented by the following Formula 2:

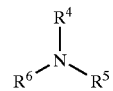

(2)

wherein $R^4$, $R^5$ and $R^6$ are the same or different, and each is alkyl, alkenyl or aryl, each optionally having a substituent group, a pair of $R^4$, $R^5$ and $R^6$ being optionally bonded to form an aliphatic or aromatic ring together with nitrogen to which each pair is bonded, or one of $R^4$, $R^5$ and $R^6$ being optionally bonded to the other two to form two-ring structure, with a hydroxycarboxylic ester represented by the following Formula 1:

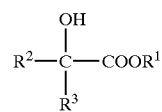

(1)

wherein $R^1$ is alkyl, alkenyl, aralkyl or aryl, $R^2$ and $R^3$ are the same or different and each is hydrogen, alkyl, alkenyl, aralkyl or aryl, thereby producing the quaternary ammonium hydroxycarboxylate represented by the following Formula 3:

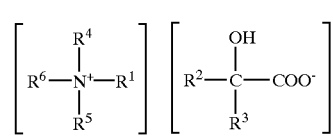

(3)

wherein $R^1$ to $R^6$ are the same as defined above.

In a second aspect of the present invention, there is provided a method for producing a mixture of quaternary ammonium hydroxycarboxylates, which comprises a step of reacting a tertiary amine represented by the following Formula 2a:

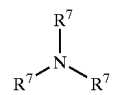

(2a)

wherein three $R^7$ groups are the same or different, and each is alkyl, alkenyl or aryl, each optionally having a substituent group, and two of three $R^7$ groups being optionally bonded to form an aliphatic or aromatic ring together with nitrogen to which each $R^7$ is bonded, with a hydroxycarboxylic ester represented by the following Formula 1':

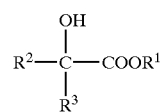

(1')

wherein $R^1$ to $R^3$ are the same as defined above, with the proviso that $R^1$ is different from at least one of three $R^7$ groups of Formula 2a, thereby producing a mixture containing at least two quaternary ammonium hydroxycarboxylates represented by the following Formula 3x:

wherein $R^1$ to $R^3$ and $R^7$ are the same as defined above, and n is an integer from 1 to 4.

In a third aspect of the present invention, there is provided a method for producing a quaternary ammonium salt of inorganic acid, which comprises:

a first step of reacting the tertiary amine 2 with the hydroxycarboxylic ester 1, thereby producing the quaternary ammonium hydroxycarboxylate 3; and a second step of reacting the quaternary ammonium hydroxycarboxylate 3 produced in the first step with an inorganic acid, thereby producing the quaternary ammonium salt of inorganic acid represented by the following Formula 5:

wherein $R^1$ and $R^4$ to $R^6$ are the same as defined above, and X is an acid radical of the inorganic acid.

In a fourth aspect of the present invention, there is provided a method for producing a mixture of quaternary ammonium salts of inorganic acid, which comprises:

a first step of reacting the tertiary amine 2a with the hydroxycarboxylic ester 1', thereby producing a mixture containing at least two quaternary ammonium hydroxycarboxylates 3x; and a second step of reacting the mixture of quaternary ammonium hydroxycarboxylates with an inorganic acid, thereby producing a mixture containing at least two quaternary ammonium salts of inorganic acid represented by the following Formula 5a:

$$[R^7{}_{4-n}N^+R^1{}_n]X^- \quad (5a)$$

wherein $R^1$, $R^7$, n and X are the same as defined above.

DETAILED DESCRIPTION OF THE INVENTION

The present invention will be described in more detail
(I) Production Method of Quaternary Ammonium Hydroxycarboxylate In the production method I, a hydroxycarboxylic ester represented by the following Formula 1:

wherein $R^1$ to $R^3$ are the same as defined above, is used as a quaternizing agent for a tertiary amine.

$R^1$ is preferably alkyl having 1 to 6 carbon atoms such as methyl, ethyl, propyl, butyl, pentyl and hexyl; alkenyl having 2 to 6 carbon atoms such as allyl; aralkyl such as benzyl; or aryl such as phenyl. Each of $R^2$ and $R^3$ is preferably hydrogen; alkyl having 1 to 6 carbon atoms such as methyl, ethyl, propyl, butyl, pentyl and hexyl; alkenyl having 2 to 6 carbon atoms such as allyl; aralkyl such as benzyl; or aryl such as phenyl.

Examples of the hydroxycarboxylic ester of Formula 1 include methyl-, ethyl-, propyl-, butyl-, pentyl-, hexyl-, benzyl-, phenyl-, and allyl esters of 2-hydroxyisobutyric acid; methyl-, ethyl-, propyl-, butyl-, pentyl-, hexyl-, benzyl-, phenyl-, and allyl esters of 2-hydroxy-2-methylbutyric acid; methyl-, ethyl-, propyl-, butyl-, pentyl-, hexyl-, benzyl-, phenyl-, and allyl esters of 2-hydroxy-2-ethylbutyric acid; methyl-, ethyl-, propyl-, butyl-, pentyl-, hexyl-, benzyl-, phenyl-, and allyl esters of lactic acid; and methyl-, ethyl-, propyl-, butyl-, pentyl-, hexyl-, allyl-, benzyl-, and phenyl esters of glycolic acid. Of the above, methyl 2-hydroxyisobutyrate is particularly preferable because it is industrially produced by a so-called modified ACH method as an intermediate in the production of methyl methacrylate.

The tertiary amine used in the production method I is represented by the following Formula 2:

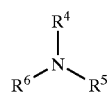

wherein $R^4$, $R^5$ and $R^6$ may be the same or different, and each is independently alkyl having 1 to 10 carbon atoms; alkenyl having 2 to 10 carbon atoms, or aryl having 6 to 10 carbon atoms. Alkyl, alkenyl and aryl may have a substituent group such as, not in the way of limitation, hydroxyl, nitro, cyano, carboxyl, formyl, alkyl, haloalkyl, and phenyl. Any pair of $R^4$, $R^5$ and $R^6$ may be bonded to each other to form an aliphatic or aromatic ring together with nitrogen, or any one of $R^4$, $R^5$ and $R^6$ may be bonded to the other two to form a bicyclic structure together with nitrogen to which $R^4$, $R^5$ and $R^6$ are bonded.

Examples of the tertiary amine of Formula 2 include aliphatic non-substituted amines such as trimethylamine, triethylamine, tripropylamine, trihexylamine, trioctylamine, tri-n-butylamine, triphenylamine, dimethylethylamine, diethylmethylamine, dimethylpropylamine, dimethyldecylamine, dimethyloctylamine, dimethylstearylamine, dimethylhexadecylamine, and N,N-dimethylaniline; aliphatic substituted amines such as N,N-dimethylethanolamine, N,N-diethylethanolamine, N,N-dibutylethanolamine, N,N-diethylnitroethylamine, and N,N-diethylcyanoethylamine; alicyclic amines such as N-ethylpyrrolidine, N-methylmorpholine, 1,5-diazabicyclo[4.3.0]-5-nonene, and 1,8-diazabicyclo[5.4.0]-7-undecene; and N-containing heterocyclic aromatic compounds such as pyridine, picoline, and N-methylimidazole.

The quaternary ammonium hydroxycarboxylate is produced according to the following reaction scheme:

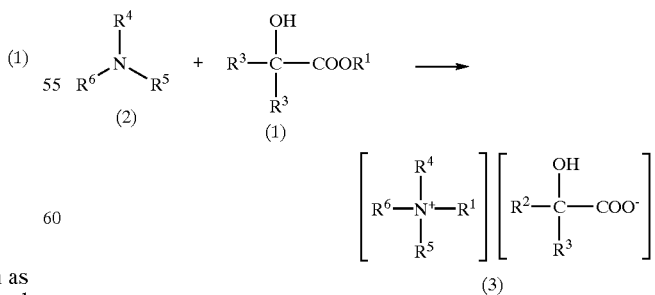

wherein $R^1$ to $R^6$ are the same as defined above.

The quaternization of the tertiary amine is generally conducted by heating the tertiary amine and the hydroxycarboxylic ester in a reaction vessel. The hydroxycarboxylic ester 1 is used in an amount of 0.01 to 100 mol, preferably 0.1 to 10 mol per one mole of the tertiary amine 2.

The manner for charging the starting compounds into a reactor is not specifically limited. In a batch-wise production, all the starting compounds may be charged at once.

The reaction temperature is not specifically limited because it depends on the types and proportion of the starting compounds, the reaction time, etc., and generally 50 to 150° C., preferably 80 to 130° C. The reaction is not completed when the reaction temperature is lower than 50° C., and a mixture of the quaternary ammonium salts is predominantly produced when higher than 150° C. The reaction pressure is not specifically limited, and the reaction proceed sufficiently under a vapor pressure of the reaction liquid itself at a reaction temperature, generally about 0 to 2 MPa (Gauge). The reaction time is usually 0.5 to 20 h, although not specifically limited because it depends on the types and proportion of the starting compounds.

The production method I proceeds sufficiently even in the absence of solvent. The reaction may be carried out also in the presence of a solvent including a polar solvent such as alcohol and an additive such as a carboxylic acid. If desired, the reaction may be carried out in an inert atmosphere of nitrogen, argon, helium, etc.

The quaternary ammonium hydroxycarboxylate 3 is separated and recovered by a known method, for example, by removing low-boiling fractions by distillation optionally followed by recrystallization. The production method I may be carried out either in batch-wise manner or in continuous manner.

(II) Production Method of Mixture of Quaternary Ammonium Hydroxycarboxylates

In the production method II, a tertiary amine represented by the following Formula 2a:

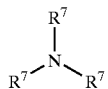

(2a)

wherein three $R^7$ groups are the same or different, and each is alkyl having 1 to 10 carbon atoms, alkenyl having 2 to 10 carbon atoms, or aryl having 6 to 10 carbon atoms, each optionally having a substituent group, and two of three $R^7$ groups being optionally bonded to form an aliphatic or aromatic ring together with nitrogen to which each $R^7$ is bonded,
is reacted with a hydroxycarboxylic ester represented by the following Formula 1':

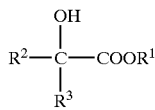

(1')

wherein $R^1$ to $R^3$ are the same as defined above, with the proviso that $R^1$ is different from at least one of three $R^7$ groups of Formula 2a,
thereby producing a mixture containing at least two quaternary ammonium hydroxycarboxylates represented by the following Formula 3x:

(3x)

wherein $R^1$ to $R^3$ and $R^7$ are the same as defined above, and n is an integer from 1 to 4, namely, a mixture of at least two quaternary ammonium hydroxycarboxylates having different quaternary ammonium ions (quaternary ammonium ions having different numbers of n). The examples of the substituent groups for $R^7$ includes the same substituents as recited with respect to $R^4$ to $R^6$, excluding the groups for forming the two-ring structure together with nitrogen.

The reaction includes the following multistage reactions:

First Step

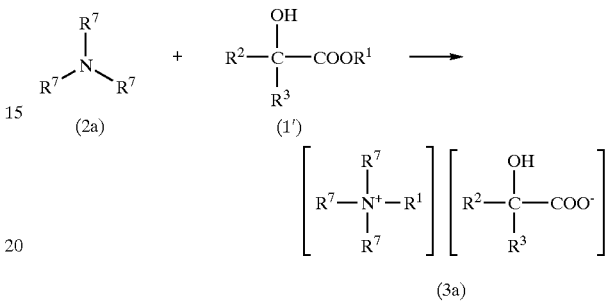

Second Step

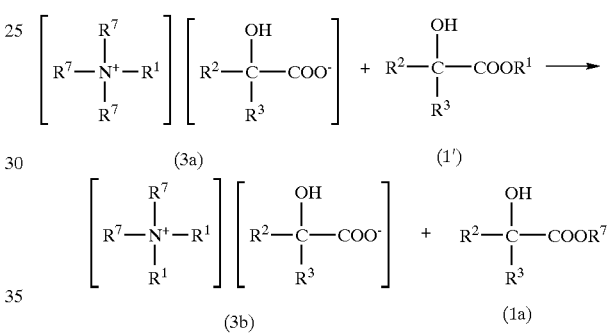

Third Step

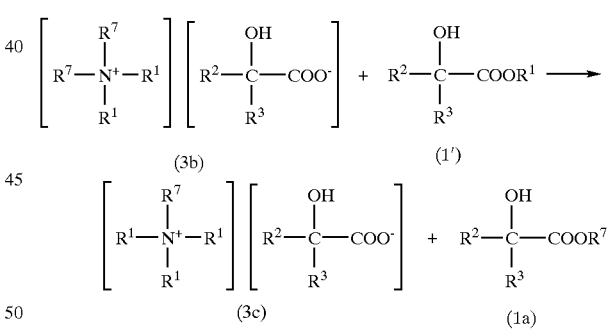

Fourth Step

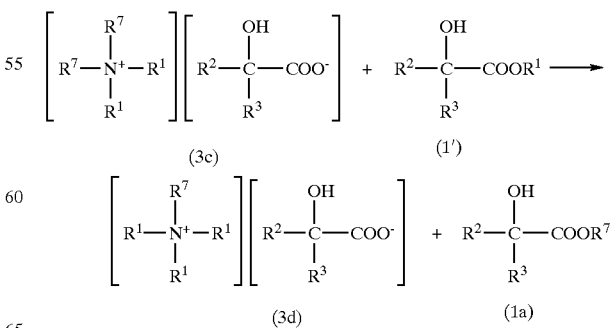

wherein $R^1$ to $R^3$ and $R^7$ are the same as defined above.

The quaternary ammonium hydroxycarboxylates 3a to 3d are collectively represented by the following Formula 3x:

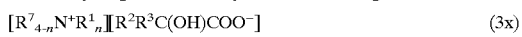

wherein $R^1$ to $R^3$, $R^7$ and n are the same as defined above.

By the reaction of the tertiary amine 2a such as trialkylamine and the hydroxycarboxylic ester 1', the quaternary ammonium hydroxycarboxylate 3a with only one $R^1$ introduced into the quaternary ammonium ion is first produced. The quaternary ammonium hydroxycarboxylate 3a further reacts with an excess of the hydroxycarboxylic ester 1' to produce the quaternary ammonium hydroxycarboxylate 3b by the replacement of one $R^7$ on the nitrogen by $R^1$ of the ester moiety. In this manner, the quaternary ammonium hydroxycarboxylates 3c and 3d are successively produced.

The above reactions are dependent on the reaction temperature, molar ratio of the starting compounds and reaction time. By suitably selecting the reaction conditions, a desired mixture of the quaternary ammonium hydroxycarboxylates can be obtained.

The reaction is generally carried out by heating the tertiary amine 2a and the hydroxycarboxylic ester 1' in a reaction vessel. One mole of the tertiary amine is reacted with 1 to 100 mol, preferably 1.5 to 10 mol of the hydroxycarboxylic ester.

Examples of the tertiary amine of Formula 2a include aliphatic non-substituted amines such as trimethylamine, triethylamine, tripropylamine, trihexylamine, trioctylamine, tri-n-butylamine, triphenylamine, dimethylethylamine, diethylmethylamine, dimethylpropylamine, dimethyldecylamine, dimethyloctylamine, dimethylstearylamine, dimethylhexadecylamine, and N,N-dimethylaniline; aliphatic substituted amines such as N,N-dimethylethanolamine, N,N-diethylethanolamine, N,N-dibutylethanolamine, N,N-diethylnitroethylamine, and N,N-diethylcyanoethylamine; alicyclic amines such as N-ethylpyrrolidine and N-methylmorpholine; and N-containing hetrocyclic aromatic compounds such as pyridine, picoline, and N-methylimidazole. Preferred are tertiary amines where three $R^7$ groups of Formula 2a are all the same, particularly, three $R^7$ groups are all the same alkyl having 2 to 10 carbon atoms, because such amines are relatively inexpensive and easily available.

The hydroxycarboxylic ester 1' is the same as the hydroxycarboxylic ester 1 used in the production method I except that $R^1$ of the ester moiety should be different from at least one of $R^7$ groups of the tertiary amine 2a. Therefore, the details of the hydroxycarboxylic ester 1' are omitted here by reference.

The manner for charging the starting compounds into a reactor is not specifically limited. In a batch-wise production, all the starting compounds may be charged at once. The reaction temperature is not specifically limited because it depends on the types and proportion of the starting compounds, the reaction time, etc., and generally 100 to 300° C., preferably 130 to 200° C., and more preferably 140 to 200° C. The mixture of quaternary ammonium hydroxycarboxylates is not obtained but only a single quaternary ammonium hydroxycarboxylate is obtained when the reaction temperature is lower than 100° C., and the yield is decreased when higher than 300° C. by decomposition. The reaction pressure is not specifically limited, and the reaction proceed sufficiently under a vapor pressure of the reaction liquid itself at a reaction temperature, generally about 0 to 2 MPa (Gauge). The reaction time is usually 0.5 to 20 h, although not specifically limited because it depends on the types and proportion of the starting compounds and the intended composition of a mixture of the quaternary ammonium salts.

Since the starting hydroxycarboxylic ester also serves as the solvent, the production method II proceeds sufficiently even in the absence of solvent without the decomposition of the hydroxycarboxylic ester. The reaction, however, may be carried out in the presence of a solvent including a polar solvent such as alcohol and an additive such as a carboxylic acid. If desired, the reaction may be carried out in an inert atmosphere of nitrogen, argon, helium, etc. The mixture of the quaternary ammonium hydroxycarboxylates is easily recovered from the reaction liquid by a known method, for example, by removing low-boiling components by distillation optionally followed by recrystallization.

(III) Production Method of Quaternary Ammonium Salt of Inorganic Acid

In the production method III, the quaternary ammonium salt of inorganic acid 5 is produced according to the following reaction scheme:

First Step

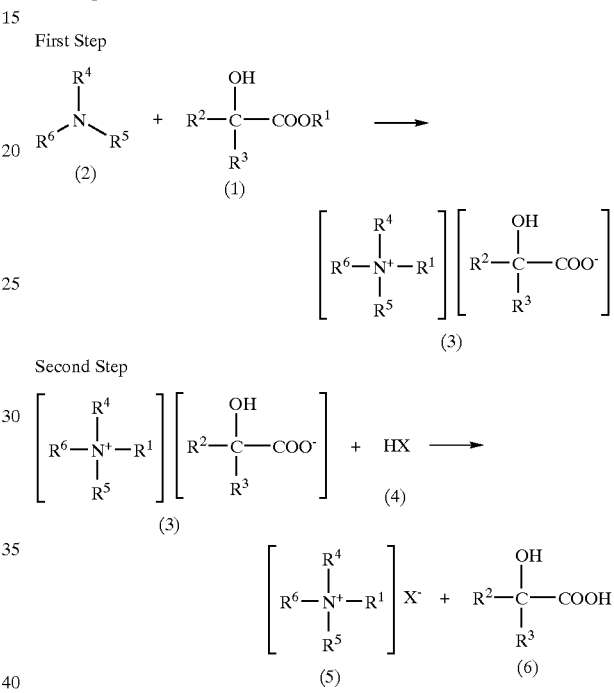

Second Step wherein $R^1$ to $R^6$ are the same as defined above, and X is an acid radical of the inorganic acid.

Since the first step is the same as the quaternization of the tertiary amine 2 with the hydroxycarboxylic ester 1 of the production method I, the details thereof are omitted here by reference.

The second step is generally carried out by dissolving the still residue from the first step into a non-aqueous solvent, and feeding the inorganic acid 4 to the resultant solution of the quaternary ammonium hydroxycarboxylate 3. The stronger the inorganic acid, the more faster the reaction proceeds. Examples of the inorganic acid include hydrogen fluoride, boron trifluoride, mixture of hydrogen fluoride and boron trifluoride, tetrafluoroboric acid, hydrogen chloride, hydrogen bromide, hydrogen iodide, nitric acid, sulfuric acid, phosphoric acid, boric acid, perchloric acid and phosphohydrofluoric acid. Tetrafluoroboric acid is an equimolar complex of boron trifluoride and hydrogen fluoride. The hydrogen fluoride/boron trifluoride mixture and tetrafluoroboric acid are preferably used for producing a quaternary ammonium slat of inorganic acid for use in electric double layer capacitor, because a solution of the quaternary ammonium salts of these acids in a non-aqueous solvent is particularly preferred as an electrolyte.

The non-aqueous solvent used in the second step is not particularly limited as far as it is inert in the reaction system. Examples thereof include alcohols such as methanol, ethanol, butanol and propanol; ketones such as acetone and methyl ethyl ketone; aromatic hydrocarbons such as benzene, toluene and xylene; and carbonic esters such as dimethyl carbonate, propylene carbonate and diethyl carbonate. The non-aqueous solvent is preferably dehydrated before use. The reaction may be carried out in an aqueous solvent using an aqueous solution of the inorganic acid.

The inorganic acid is used in an amount of 0.8 to 1.2 mol, preferably 0.95 to 1.05 per one mole of the quaternary ammonium hydroxycarboxylate. The reaction is not completed when the amount is less than 0.8 mol. When exceeding 1.2 mol, the hydroxycarboxylic acid that is by-produced simultaneously with the formation of the quaternary ammonium salt of inorganic acid is likely to be decomposed. The second step is carried out, but not particularly limited, at room temperature under atmospheric pressure. The reaction time is generally 0.02 to 20 h, preferably 0.1 to 5 h.

The quaternary ammonium salt of inorganic acid is easily removed from the reaction liquid and purified by a known method, for example, by removing low-boiling components by distillation optionally followed by recrystallization. The hydroxycarboxylic acid by-produced in the second step is recovered by distillation, etc., and can be reused after converted into ester to improve the production economy. The filtrate from the recrystallization can be used in the subsequent filtration step or other steps after condensed or discarding, if necessary, a portion thereof.

(IV) Production Method of Mixture of Quaternary Ammonium Salts of Inorganic Acid In the production method IV, the quaternary ammonium salts of inorganic acid are produced according to the following reaction scheme:

First Step

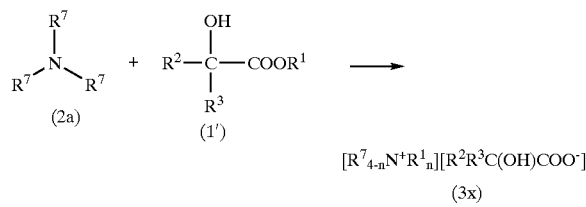

Second Step

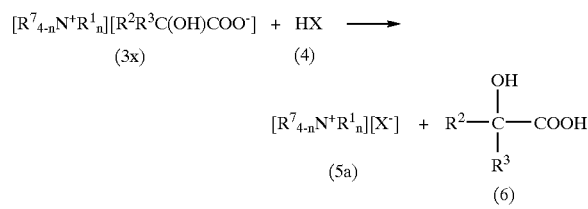

wherein $R^1$ to $R^3$, $R^7$, n and X are the same as defined above.

The first step of the production method IV is the same as the production method II, and the details thereof are omitted here by reference. Also, the second step of the production method IV is the same as the second step of the production method III except for using a mixture of quaternary ammonium hydroxycarboxylates 3x as the starting material, and the details thereof are also omitted here by reference.

The present invention will be described in further detail by way of the following examples. However, it should be noted that the scope of the present invention is not limited to the following examples. Each starting compound was dehydrated before use. The products obtained were analyzed by $^1$H-NMR, $^{13}$C-NMR and ion chromatography. The moisture content was determined by Karl Fischer's moisture meter.

EXAMPLE 1

Into a 100-mL SUS316 shaking autoclave, were charged 10 g (0.1 mol) of triethylamine and 59 g (0.5 mol) of methyl 2-hydroxyisobutyrate as a quaternizing agent, and the autoclave was shaken. After the contents of the autoclave reached 120° C., the temperature was kept there for 8 h to proceed the reaction. The reaction pressure was 0.1 MPa. After the reaction was completed, the reaction liquid was cooled and distilled to remove low-boiling components, thereby obtaining triethylmethylammonium 2-hydroxyisobutyrate at 87.4 mol % yield based on triethylamine. No decomposed product of methyl 2-hydroxyisobutyrate was detected in the gas chromatographic analysis on the distillate.

EXAMPLE 2

The reaction of Example 1 was repeated except for using 6.0 g (0.1 mol) of trimethylamine in place of triethylamine. After the reaction was completed, low-boiling components were removed by distillation to obtain tetramethylammonium 2-hydroxyisobutyrate at 85.4 mol % yield based on trimehylamine.

EXAMPLE 3

The reaction of Example 1 was repeated expect for using 8.7 g (0.1 mol) of diethylmethylamine in place of triethylamine. After the reaction was completed, low-boiling components were removed by distillation to obtain diethyldimethylammonium 2-hydroxyisobutyrate at 82.1 mol % yield based on diethylmethylamine.

COMPARATIVE EXAMPLE 1

The reaction of Example 1 was repeated except for using 45 g (0.5 mol) of dimethyl carbonate as a quaternizing agent in place of methyl 2-hydroxyisobutyrate. The reaction pressure was increased as the reaction proceeded and reached 3.5 MPa after 5 h as a result of the generation of carbon dioxide gas and methanol due to the decomposition of dimethyl carbonate.

COMPARATIVE EXAMPLE 2

The reaction of Example 1 was repeated except for using 37 g (0.5 mol) of methyl acetate as a quaternizing agent in place of methyl 2-hydroxyisobutyrate. After the reaction was completed, low-boiling components were removed by distillation to obtain triethylmethylammonium acetate at 3.2 mol % yield based on triethylamine.

EXAMPLE 4

Into a 5-L SUS316 autoclave equipped with an electromagnetic stirrer, were charged 1010 g (10 mol) of triethylamine and 5900 g (50 mol) of methyl 2-hydroxyisobutyrate, and heated under stirring. After the contents of the autoclave reached 160° C., the temperature was kept there for 4 h to proceed the reaction. The reaction pressure was 0.3 MPa (Gauge). After the reaction was completed, the reaction liquid was cooled and low-boiling components were removed from the reaction liquid by distillation to obtain 2026 g of a pale brown still residue. The analysis of the still residue showed that the product was a mixture of 62.3% by weight of triethylmethylammonium 2-hydroxyisobutyrate, 33.7% by weight of diethyldimethylammonium 2-hydroxyisobutyrate and 4.0% by weight of ethyltrimethylammonium 2-hydroxyisobutyrate. The yield was 95.2 mol % in total based on triethylamine.

EXAMPLE 5

The reaction was carried out in the same manner as in Example 4 except for changing the reaction temperature to 150° C. and the reaction time to 4 h. The analysis of the still residue (1945 g) showed that the product was a mixture of 84% by weight of triethylmethylammonium 2-hydroxyisobutyrate and 16% by weight of diethyldimethylammonium 2-hydroxyisobutyrate. The yield was 89.8 mol % in total based on triethylamine.

EXAMPLE 6

The reaction was carried out in the same manner as in Example 5 except for changing the reaction temperature to 140° C. and the reaction time to 6 h. The analysis of the still residue (1897 g) showed that the product was a mixture of 96% by weight of triethylmethylammonium 2-hydroxyisobutyrate and 4% by weight of diethyldimethylammonium 2-hydroxyisobutyrate. The yield was 86.9 mol % in total based on triethylamine.

EXAMPLE 7

First Step

Into a 5-L SUS316 autoclave equipped with an electromagnetic stirrer, were charged 505 g (5.0 mol) of triethylamine and 2950 g (25 mol) of methyl 2-hydroxyisobutyrate, and heated under stirring. After the contents of the autoclave reached 120° C., the temperature was kept there for 8 h to proceed the reaction. The reaction pressure was 0.1 MPa (Gauge). After the reaction was completed, the reaction liquid was cooled and low-boiling components were removed from the reaction liquid by distillation to obtain triethylmethylammonium 2-hydroxyisobutyrate in 87.4 mol % yield based on triethylamine.

Second Step

To 64 g (1.4 mol) of ethanol in a 200-mL Hastelloy C-made HF-BF3 mixer equipped with a stirrer, was added dropwise 10 g (0.5 mol) of anhydrous hydrogen fluoride at ordinary pressure while cooling at 5° C. Then, by introducing 33 g (0.5 mol) of boron trifluoride gas, an ethanol solution of tetrafluoroboric acid was prepared. Separately, into a 500-mL Hastelloy C-made reactor equipped with a stirrer, were charged 110 g (0.5 mol) of triethylmethylammonium 2-hydroxyisobutyrate prepared in the first step and 88 g (1.9 mol) of ethanol, thereby preparing an ethanol solution of triethylmethylammonium 2-hydroxyisobutyrate.

The ethanol solution of tetrafluoroboric acid was added dropwise to the ethanol solution of triethylmethylammonium 2-hydroxyisobutyrate over 30 min at 20° C. under ordinary pressure. After the addition, the stirring was continued for one hour. No generation of gas was detected during the reaction. The resultant slurry was directly filtered. The filtration cake was rinsed with a small portion of ethanol and vacuum dried to obtain 90 g (0.44 mol) of triethylmethylammoniumu tetrafluoroborate as white crystal. The ion chromatographic analysis showed that the purity of the obtained crystal was 99.5% by weight and the yield was 89 mol % based on triethylmethylammonium 2-hydroxyisobutyrate. The crystal had a moisture content of 100 ppm or less and a fluoride ion content of 50 ppm or less. The ICP metal analysis showed that the content was lower than the detection limits (1 ppm) for any heavy metals.

EXAMPLE 8

The reaction was carried out in the same manner as in Example 7 except for using in the second step 105 g (0.5 mol) of a 42% aqueous solution of tetrafluoroboric acid in place of the ethanol solution thereof, and 110 g (6.1 mol) of an aqueous solution of triethylmethylammonium 2-hydroxyisobutyrate in place of the ethanol solution thereof. No generation of gas due to by-production was observed, and the reaction liquid was homogeneous. The still residue after evaporation of the reaction liquid to dryness was recrystallized from ethanol and vacuum dried to obtain 89 g (0.44 mol) of triethylmethylammonium tetrafluoroborate. The purity was 99.0% by weight, the yield was 88.7 mol % based on triethylmethylammonium 2-hydroxyisobutyrate, and the moisture content of the crystal was 360 ppm.

EXAMPLE 9

First Step

Into a 5-L SUS316 autoclave equipped with an electromagnetic stirrer, were charged 1010 g (10 mol) of triethylamine and 5900 g (50 mol) of methyl 2-hydroxyisobutyrate, and heated under stirring. After the contents of the autoclave reached 160° C., the temperature was kept there for 4 h to proceed the reaction. The reaction pressure was 0.3 MPa (Gauge). After the reaction was completed, the reaction liquid was cooled and low-boiling components were removed from the reaction liquid by distillation to obtain 2026 g of a pale brown still residue. The analysis of the still residue showed that the product was a mixture of 62.3% by weight of triethylmethylammonium 2-hydroxyisobutyrate, 33.7% by weight of diethyldimethylammonium 2-hydroxyisobutyrate and 4.0% by weight of ethyltrimethylammonium 2-hydroxyisobutyrate. The yield was 95.2 mol % based on triethylamine.

Second Step

To 64 g (1.4 mol) of ethanol in a 200-mL Teflon-lining HF-BF3 mixer equipped with a stirrer, was added dropwise 10 g (0.5 mol) of anhydrous hydrogen fluoride at ordinary pressure while cooling at 5° C. Then, by introducing 33 g (0.5 mol) of boron trifluoride gas, an ethanol solution of tetrafluoroboric acid was prepared. Separately, into a 500-mL Teflon-lining reactor equipped with a stirrer, were charged 106 g (0.5 mol in total) of the mixture of triethylmethylammonium-, diethyldimethylammonium- and ethyltrimethylammonium 2-hydroxyisobutyrates prepared in the first step and 88 g (1.9 mol) of ethanol, thereby preparing an ethanol solution of the mixture of quaternary ammonium 2-hydroxyisobutyrates.

The ethanol solution of tetrafluoroboric acid was added dropwise to the ethanol solution of the mixture of quaternary ammonium 2-hydroxyisobutyrates over 30 min at 20° C. under ordinary pressure. After the addition, the stirring was continued for one hour. The resultant slurry was directly filtered. The filtration cake was rinsed with a small portion of ethanol and vacuum dried to obtain 89.5 g of white crystals. The analysis on the crystals showed that the product was a mixture of 66% by weight of triethylmethylammonium tetrafluoroborate, 30% by weight of diethyldimethylammonium tetrafluoroborate and 4% by weight of ethyltrimethylammonium tetrafluoroborate. The total yield of the mixture was 90.5 mol % based on the mixture of quaternary ammonium 2-hydroxyisobutyrates. The crystal had a moisture content of 100 ppm or less and a fluoride ion content of 50 ppm or less. The metal analysis showed that the content was lower than the detection limits (1 ppm) for any heavy metals.

EXAMPLE 10

The reaction was carried out in the same manner as in Example 9 except for using in the second step 105 g (0.5 mol) of a 42% aqueous solution of tetrafluoroboric acid in place of the ethanol solution thereof, and 110 g (6.1 mol) of an aqueous solution of the mixture of quaternary ammonium 2-hydroxyisobutyrates in place of the ethanol solution thereof. The reaction liquid was homogeneous. The still residue after evaporation of the reaction liquid to dryness was recrystallized from ethanol and vacuum dried to obtain 87 g of a mixture of 66% by weight of triethylmethylammonium tetrafluoroborate, 32% by weight of diethyldimethylammonium tetrafluoroborate and 2.0% by weight of ethyltrimethylammonium tetrafluoroborate. The total yield of the mixture was 88.7 mol % based on the mixture of quaternary ammonium 2-hydroxyisobutyrates, and the moisture content of the crystal was 600 ppm.

EXAMPLE 11

The first step of Example 9 was repeated except for changing the reaction temperature to 150° C. and the reaction time to 4 h. The analysis on the still residue (1945 g) showed that the product was a mixture of 84% by weight of triethylmethylammonium 2-hydroxyisobutyrate and 16% by weight of diethyldimethylammonium 2-hydroxyisobutyrate. The total yield was 89.8 mol % based on triethylamine.

The second step of Example 9 was repeated except for charging into the reactor 108 g (0.5 mol in total) of the mixture of quaternary ammonium salts obtained in the first step. The analysis on the obtained crystals showed that the product was a mixture of 86% by weight of triethylmethylammonium tetrafluoroborate and 14% by weight of diethyldimethylammonium tetrafluoroborate. The total yield of the mixture was 91.2 mol % based on the mixture of quaternary ammonium 2-hydroxyisobutyrates. The crystal had a moisture content of 100 ppm or less and a fluoride ion content of 50 ppm or less. The metal analysis showed that the content was lower than the detection limits (1 ppm) for any heavy metals.

EXAMPLE 12

The first step of Example 9 was repeated except for changing the reaction temperature to 140° C. and the reaction time to 6 h. The analysis on the still residue (1897 g) showed that the product was a mixture of 96% by weight of triethylmethylammonium 2-hydroxyisobutyrate and 4% by weight of diethyldimethylammonium 2-hydroxyisobutyrate. The total yield was 86.9 mol % based on triethylamine.

The second step of Example 9 was repeated except for charging into the reactor 109 g (0.5 mol in total) of the mixture of quaternary ammonium salts obtained in the first step. The analysis on the obtained crystals showed that the product was a mixture of 97% by weight of triethylmethylammonium tetrafluoroborate and 3% by weight of diethyldimethylammonium tetrafluoroborate. The total yield of the mixture was 93 mol % based on the mixture of quaternary ammonium 2-hydroxyisobutyrates. The crystal had a moisture content of 100 ppm or less and a fluoride ion content of 50 ppm or less. The metal analysis showed that the content was lower than the detection limits (1 ppm) for any heavy metals.

As described above, according to the production method of the present invention using a hydroxycarboxylic ester as a quaternizing agent, a tertiary amine is easily quaternized without using a solvent and a highly pure quaternary ammonium salt can be produced in industrially advantageous manner. Therefore, the method is of great industrial value. In addition, by suitably controlling the reaction conditions, a mixture of quaternary ammonium hydroxycarboxylates can be produced in industrially advantageous manner by the quaternization of only one tertiary amine with a hydroxycarboxylic ester without the decomposition of the hydroxycarboxylic ester.

Additionally, the production method of the present invention can produce a highly pure quaternary ammonium salt of inorganic acid suitable for use as an electrolyte at high yields in industrially advantageous manner, the method including a fist step where the reaction proceeds with a sufficient speed under a low pressure without using a solvent, and a second step where the generation of by-produced carbon dioxide is avoided. Therefore, the method is of great industrial value. In addition, by suitably controlling the reaction conditions of the first step, a mixture of quaternary ammonium hydroxycarboxylates can be produced from the quaternization of only one tertiary amine with a hydroxycarboxylic ester without causing the decomposition of the hydroxycarboxylic ester. By reacting the mixture with an inorganic acid in the second step, a mixture of quaternary ammonium salts of inorganic acid can be produced in industrially advantageous manner without changing the proportion of the starting mixture of quaternary ammonium hydroxycarboxylates.

What is claimed is:

1. A method for producing a quaternary ammonium salt of inorganic acid, which comprises:

a step of reacting a tertiary amine represented by the following Formula 2:

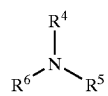

(2)

wherein $R^4$, $R^5$ and $R^6$ are the same or different, and each is alkyl, alkenyl or aryl, each optionally having a substituent group, a pair of $R^4$, $R^5$ and $R^6$ being optionally bonded to form an aliphatic or aromatic ring together with nitrogen to which the pair are bonded, or one of $R^4$, $R^5$ and $R^6$ being optionally bonded to the other two to form two-ring structure, with a hydroxycarboxylic ester represented by the following Formula 1:

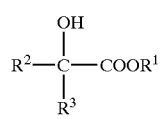

(1)

wherein $R^1$ is alkyl, alkenyl, aralkyl or aryl, $R^2$ and $R^3$ are the same or different and each is hydrogen, alkyl, alkenyl, aralkyl or aryl, thereby producing the quaternary ammonium hydroxycarboxylate represented by the following Formula 3:

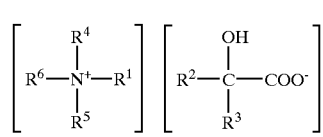

(3)

wherein $R^1$ to $R^6$ are the same as defined above; and a step of reacting the quaternary ammonium hydroxycarboxylate represented by the Formula 3 with an inorganic acid, thereby producing the quaternary ammonium salt of inorganic acid represented by the following Formula 5:

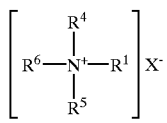  (5)

wherein $R^1$ and $R^4$ to $R^6$ are the same as defined above, and X is an acid radical of the inorganic acid, the inorganic acid being at least one acid selected from the group consisting of hydrogen fluoride, boron trifluoride, mixture of hydrogen fluoride and boron trifluoride, tetrafluoroboric acid, hydrogen chloride, hydrogen bromide, hydrogen iodide, nitric acid, sulfuric acid, phosphoric acid, boric acid, perchloric acid and phosphohydrofluoric acid.

2. The method according to claim 1, wherein the hydroxycarboxylic ester is methyl 2-hydroxyisobutyrate.

3. The method according to claim 1, wherein the tertiary amine and the hydroxycarboxylic ester are reacted in the absence of solvent.

4. The method according to claim 1, wherein 0.01 to 100 mol of the hydroxycarboxylic ester is reacted with one mole of the tertiary amine.

5. The method according to claim 1, wherein the tertiary amine and the hydroxycarboxylic ester are reacted at 50 to 150° C. under 0 to 2 MPa (Gauge) for 0.5 to 20 h.

6. The method according to claim 1, wherein the inorganic acid is tetrafluoroboric acid or the mixture of hydrogen fluoride and boron trifluoride.

7. The method according to claim 1, wherein the starting materials are substantially free from water.

8. The method according to claim 1, wherein 0.8 to 1.2 mol of the inorganic acid is reacted with one mole of the quaternary ammonium hydroxycarboxylate.

9. The method according to claim 1, wherein the quaternary ammonium hydroxycarboxylate and the inorganic acid are reacted at room temperature under atmospheric pressure for 0.02 to 20 h.

10. A method for producing a mixture of quaternary ammonium hydroxycarboxylates, which comprises a step of reacting a tertiary amine represented by the following Formula 2a:

  (2a)

wherein three $R^7$ groups are the same or different, and each is alkyl, alkenyl or aryl, each optionally having a substituent group, and two of three $R^7$ group being optionally bonded to form an aliphatic or aromatic ring together with nitrogen to which each $R^7$ is bonded,
with a hydroxycarboxylic ester represented by the following Formula 1':

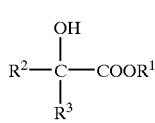  (1')

wherein $R^1$ is alkyl, alkenyl, aralkyl or aryl, $R^2$ and $R^3$ are the same or different and each is hydrogen, alkyl, alkenyl, aralkyl or aryl, with the proviso that $R^1$ is different from at least one of three $R^7$ groups of Formula 2a, thereby producing a mixture containing at least two quaternary ammonium hydroxycarboxylates represented by the following Formula 3x:

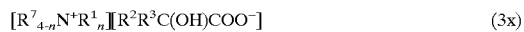  (3x)

wherein $R^1$ to $R^3$ and $R^7$ are the same as defined above, and n is an integer from 1 to 4.

11. The method according to claim 10, wherein the hydroxycarboxylic ester is methyl 2-hydroxyisobutyrate.

12. The method according to claim 10, wherein $R^7$ is ethyl and $R^1$ is methyl.

13. The method according to claim 10, wherein the tertiary amine is at least one amine selected from the group consisting of trimethylamine, triethylamine, tripropylamine, trihexylamine, trioctylamine, tri-n-butylamine and triphenylamine.

14. The method according to claim 10, wherein the tertiary amine and the hydroxycarboxylic ester are reacted in the absence of solvent.

15. The method according to claim 10, wherein 1 to 100 mol of the hydroxycarboxylic ester is reacted with one mole of the tertiary amine.

16. The method according to claim 10, wherein the tertiary amine and the hydroxycarboxylic ester are reacted at 100 to 300° C. under 0 to 2 MPa (Gauge) for 0.5 to 20 h.

17. A method for producing a mixture of quaternary ammonium salts of inorganic acid, which comprises a step of reacting a mixture of quaternary ammonium hydroxycarboxylates produced by the method as defined in claim 10 with an inorganic acid, thereby producing a mixture containing at least two quaternary ammonium salts of inorganic acid represented by the following Formula 5a:

  (5a)

wherein $R^1$, $R^7$, and n are the same as defined above, and X is an acid radical of the inorganic acid.

18. The method according to claim 17, wherein the inorganic acid is at least one acid selected from the group consisting of hydrogen fluoride, boron trifluoride, mixture of hydrogen fluoride and boron trifluoride, tetrafluoroboric acid, hydrogen chloride, hydrogen bromide, hydrogen iodide, nitric acid, sulfuric acid, phosphoric acid, boric acid, perchloric acid and phosphohydrofluoric acid.

19. The method according to claim 17, wherein the inorganic acid is tetrafluoroboric acid or the mixture of hydrogen fluoride and boron trifluoride.

20. The method according to claim 17, wherein the starting materials are substantially free from water.

21. The method according to claim 17, wherein 0.8 to 1.2 mol of the inorganic acid is reacted with one mole of the quaternary ammonium hydroxycarboxylate.

22. The method according to claim 17, wherein the quaternary ammonium hydroxycarboxylate and the inorganic acid are reacted at room temperature under atmospheric pressure for 0.02 to 20 h.

23. A method for producing a quaternary ammonium salt of inorganic acid, which comprises:
a step of reacting a tertiary amine represented by the following Formula 2:

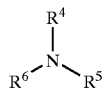  (2)

wherein $R^4$, $R^5$ and $R^6$ are the same or different, and each is alkyl, alkenyl or aryl, each optionally having a substituent group, a pair of $R^4$, $R^5$ and $R^6$ being optionally bonded to form an aliphatic or aromatic ring together with nitrogen to which the pair are bonded, or one of $R^4$, $R^5$ and $R^6$ being optionally bonded to the other two to form two-ring structure, with a hydroxycarboxylic ester represented by the following Formula 1:

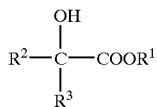

(1)

wherein $R^1$ is alkyl, alkenyl, aralkyl or aryl, $R^2$ and $R^3$ are the same or different and each is hydrogen, alkyl, alkenyl, aralkyl or aryl, thereby producing the quaternary ammonium hydroxycarboxylate represented by the following Formula 3:

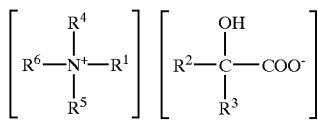

(3)

wherein $R^1$ to $R^6$ are the same as defined above; and a step of reacting the quaternary ammonium hydroxycarboxylate represented by the Formula 3 with an inorganic acid, thereby producing the quaternary ammonium salt of inorganic acid represented by the following Formula 5:

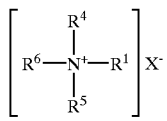

(5)

wherein $R^1$ and $R^4$ to $R^6$ are the same as defined above, and X is an acid radical of the inorganic acid, and wherein the starting materials are substantially free of water.

24. A method for producing a quaternary ammonium salt of inorganic acid, which comprises:

a step of reacting a tertiary amine represented by the following Formula 2:

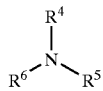

(2)

wherein $R^4$, $R^5$ and $R^6$ are the same or different, and each is alkyl, alkenyl or aryl, each optionally having a substituent group, a pair of $R^4$, $R^5$ and $R^6$ being optionally bonded to form an aliphatic or aromatic ring together with nitrogen to which the pair are bonded, or one of $R^4$, $R^5$ and $R^6$ being optionally bonded to the other two to form two-ring structure, with a hydroxycarboxylic ester represented by the following Formula 1:

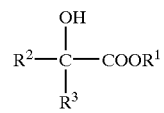

(1)

wherein $R^1$ is alkyl, alkenyl, aralkyl or aryl, $R^2$ and $R^3$ are the same or different and each is hydrogen, alkyl, alkenyl, aralkyl or aryl, thereby producing the quaternary ammonium hydroxycarboxylate represented by the following Formula 3:

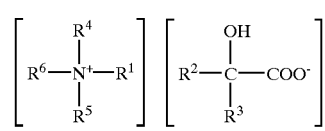

(3)

wherein $R^1$ to $R^6$ are the same as defined above; and a step of reacting the quaternary ammonium hydroxycarboxylate represented by the Formula 3 with an inorganic acid, thereby producing the quaternary ammonium salt of inorganic acid represented by the following Formula 5:

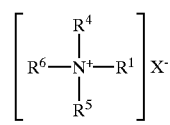

(5)

wherein $R^1$ and $R^4$ to $R^6$ are the same as defined above, and X is an acid radical of the inorganic acid, and wherein 0.8 to 1.2 mol of the inorganic acid is reacted with one mole of the quaternary ammonium hydroxycarboxylate.

25. A method for producing a quaternary ammonium salt of inorganic acid, which comprises:

a step of reacting a tertiary amine represented by the following Formula 2:

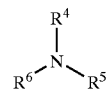

(2)

wherein $R^4$, $R^5$ and $R^6$ are the same or different, and each is alkyl, alkenyl or aryl, each optionally having a substituent group, a pair of $R^4$, $R^5$ and $R^6$ being optionally bonded to form an aliphatic or aromatic ring together with nitrogen to which the pair are bonded, or one of $R^4$, $R^5$ and $R^6$ being optionally bonded to the other two to form two-ring structure, with a hydroxycarboxylic ester represented by the following Formula 1:

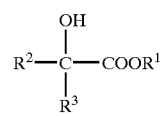

(1)

wherein $R^1$ is alkyl, alkenyl, aralkyl or aryl, $R^2$ and $R^3$ are the same or different and each is hydrogen, alkyl, alkenyl, aralkyl or aryl, thereby producing the quaternary ammonium hydroxycarboxylate represented by the following Formula 3:

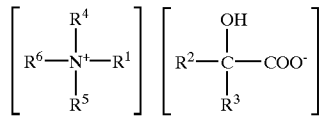 (3)

wherein R1 to R6 are the same as defined above; and a step of reacting the quaternary ammonium hydroxycarboxylate represented by the Formula 3 with an inorganic acid, thereby producing the quaternary ammonium salt of inorganic acid represented by the following Formula 5:

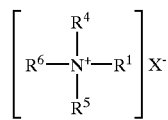 (5)

wherein $R^1$ and $R^4$ to $R^6$ are the same as defined above, and X is an acid radical of the inorganic acid, and wherein the quaternary ammonium hydroxycarboxylate and the inorganic acid are reacted at room temperature under atmospheric pressure for 0.02 to 20 h.

* * * * *